US00PP27685P3

(12) United States Plant Patent
Hachmann

(10) Patent No.: US PP27,685 P3
(45) Date of Patent: Feb. 21, 2017

(54) ***DASIPHORA* PLANT NAMED 'HACHDON'**

(50) Latin Name: ***Dasiphora fruticosa* subsp. *fruticosa***
Varietal Denomination: Hachdon

(71) Applicant: Holger Hachmann, Barmstedt (DE)

(72) Inventor: Holger Hachmann, Barmstedt (DE)

(73) Assignee: HACHMANN BAUMSCHULEN, Barmstedt (DE)

( * ) Notice: Subject to any disclaimer, the term of this patent is extended or adjusted under 35 U.S.C. 154(b) by 118 days.

(21) Appl. No.: 14/544,419

(22) Filed: Jan. 5, 2015

(65) Prior Publication Data

US 2016/0198606 P1 Jul. 7, 2016

(51) Int. Cl.
*A01H 5/02* (2006.01)

(52) U.S. Cl.
USPC ..... Plt./237

(58) Field of Classification Search
USPC ..... Plt./237, 263.1
See application file for complete search history.

(56) References Cited

PUBLICATIONS

CPVO Community Plant Variety Office Feb. 2014, Apr. 15, 2014 retrieved on Jun. 21, 2016, retrieved from the Internet at <http://www.cpvo.europa.eu/documents/gazettes/2014/cpvo_2014_2.pdf> pp. cover page, 32 and 52.*

Plant Varieties Journal Apr. 2014/No. 91, retrieved on Jun. 21, 2016, retrieved from the Internet at <http://publications.gc.ca/collections/collection_2014/acia-cfia/A27-13-91-eng.pdf> 3 pp.*

* cited by examiner

*Primary Examiner* — June Hwu
(74) *Attorney, Agent, or Firm* — Penny J. Aguirre

(57) ABSTRACT

A new cultivar of *Dasiphora* plant, 'Hachdon', that is characterized by its well-branched, bushy, dwarf plant habit, its very floriferous blooming habit; blooming from July to September in Germany, its flowers that are deep orange in color and non-fading, and its resistance to powdery mildew and red spider mites.

2 Drawing Sheets

Botanical classification: *Dasiphora fruticosa* subsp. *fruticosa.*

Variety denomination: 'Hachdon'.

BACKGROUND OF THE INVENTION

The present invention relates to a new and distinct cultivar of *Dasiphora fruticosa* subsp. *fruiticosa*. The new cultivar will be referred to hereafter by its cultivar name, 'Hachdon'. 'Hachdon' is a new cultivar of shrubby cinquefoil grown for use as a landscape shrub.

The new cultivar is the result of a controlled breeding program conducted by the Inventor in Barmstedt, Germany. The intent of the breeding program is to develop new cultivars of *Dasiphora* with brightly colored flowers. The new cultivar arose from a cross made by the Inventor in Barmstedt, Germany in summer of 2003 between the cultivars 'Annette' (not patented) as the female parent and 'Orangeschimmer' (not patented) as the male parent. The Inventor selected 'Hachdon' as a single unique plant amongst the seedlings that resulted from the above cross in July of 2006.

Asexual propagation of the new cultivar was first accomplished by the Inventor by softwood stem cuttings in Barmstedt, Germany in 2012. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hachdon' as a unique cultivar of *Dasiphora.*

1. 'Hachdon' exhibits a well-branched, bushy, dwarf plant habit.
2. 'Hachdon' exhibits a very floriferous blooming habit; blooming from July to September in Germany.
3. 'Hachdon' exhibits flowers that are deep orange in color and non-fading.
4. 'Hachdon' has been observed to be resistant to powdery mildew (*Podosphaera aphanis*) and red spider mites (*Tetranychus urticae*).

The female parent of 'Hachdon', 'Annette', differs from 'Hachdon' in having flowers that are lighter in color, in having an upright plant habit, and in having a less floriferous flowering habit. The male parent of 'Hachdon', 'Orangeschimmer', differs from 'Hachdon' in having a less floriferous blooming habit, in having a more vigorous growth rate, and in having flowers that are smaller in size. 'Hachdon' can be most closely compared to the cultivars 'Tangerine' (not patented) and 'Orangeade' (not patented). 'Tangerine' differs from 'Hachdon' in having flowers that are yellow-orange in color and quickly fade, in having an upright plant habit, and in having a less floriferous blooming habit. 'Orangeade' differs from 'Hachdon' in having orange colored flowers that fade quickly after opening to yellow-orange, in having a more vigorous growth rate, and in having a broadly upright plant shape.

BRIEF DESCRIPTION OF THE DRAWINGS

The accompanying colored photographs illustrate the overall appearance and distinct characteristics of the new cultivar, 'Hachdon'. The photographs were taken of two year-old plants as grown outdoors in two-liter containers in Barmstedt, Germany.

The photograph in FIG. 1 provides a view of the overall plant habit of 'Hachdon'.

Figure 1:
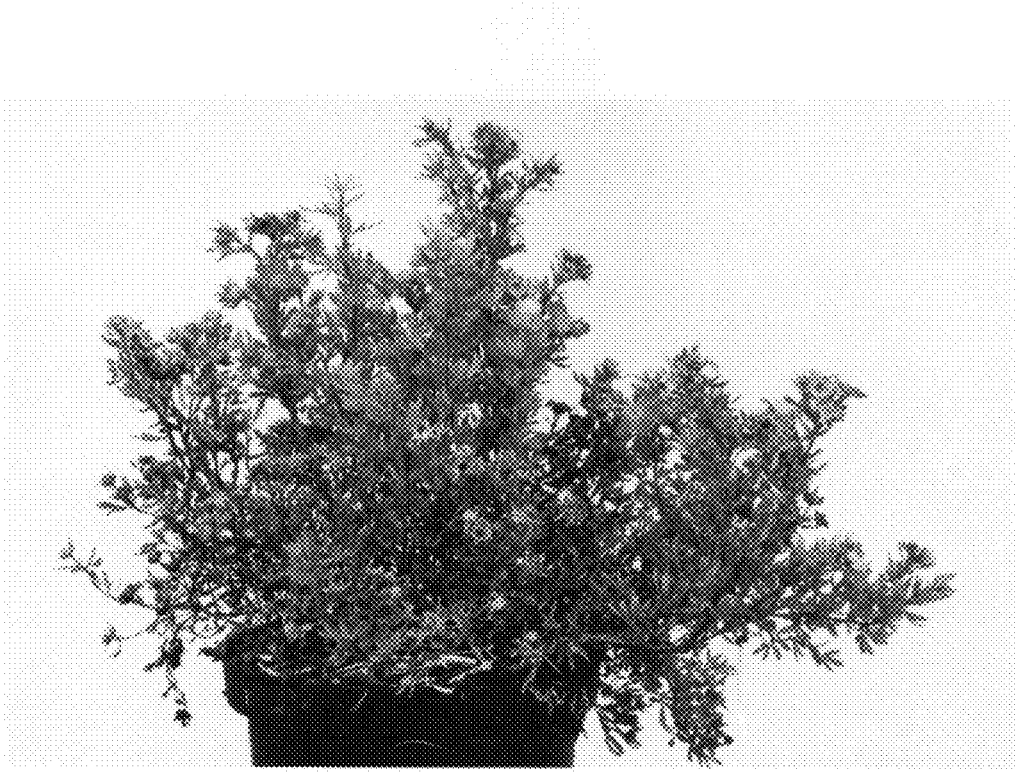
Figure 2:
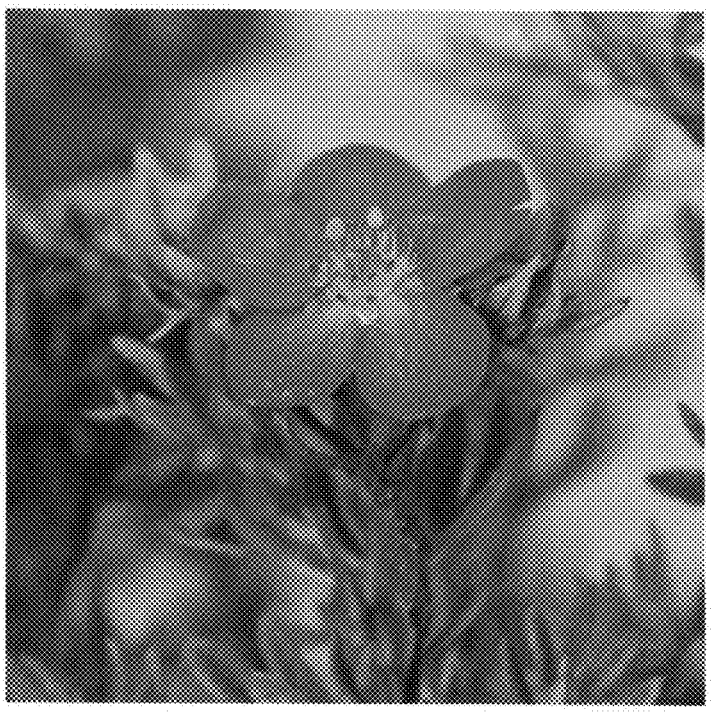

The photograph in FIG. 2 provides a close-up view of a mature flower of 'Hachdon'.

Figure 3:
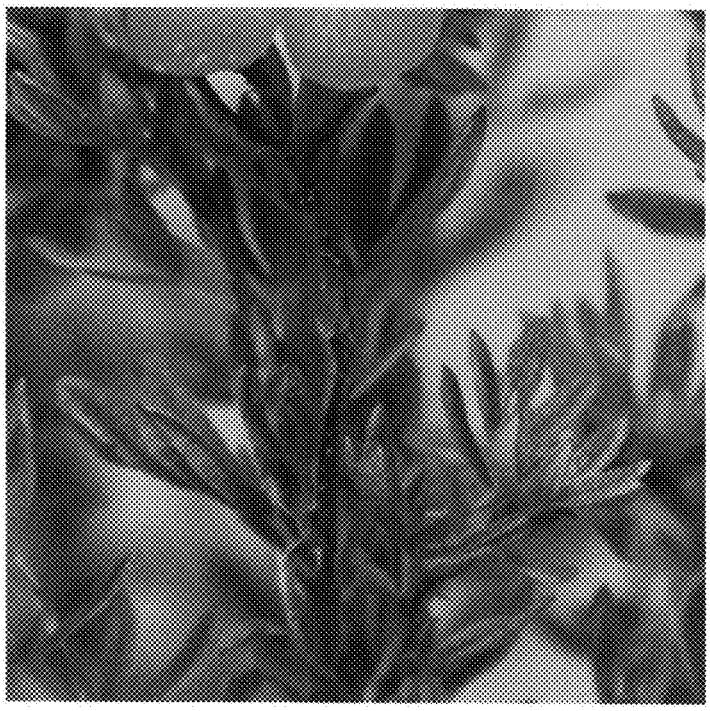

The photograph in FIG. 3 provides a close-up view of the foliage of 'Hachdon'.

The colors in the photographs are as close as possible with digital photography techniques available, the color values cited in the detailed botanical description accurately describe the colors of the new *Dasiphora*.

DETAILED BOTANICAL DESCRIPTION

The following is a detailed description of two year-old plants of the new cultivar as grown outdoors in two-liter containers in Barmstedt, Germany. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Twelve weeks from July to September/October in Barmstedt, Germany.

*Plant type*.—Perennial, deciduous shrub.

*Plant habit*.—Well-branched, dwarf, bushy plant habit.

*Height and spread*.—An average of 60 cm height and 90 cm in width.

*Cold hardiness*.—At least to U.S.D.A. Zone 3.

*Diseases and pests*.—Resistance to powdery mildew (*Podosphaera aphanis*) and red spider mites (*Tetranychus urticae*) has been observed.

*Propagation*.—Softwood stem cuttings.

*Root description*.—Fibrous and fine.

*Growth rate*.—Slow.

*Crop time to produce a flowering plant*.—About 15 months from a rooted cutting to fully develop a flowering plant in a 2-liter container.

Branch description:

*Stem shape*.—Rounded.

*Stem color*.—Young; 145B to 145C tinged with 186C to 186D, mature wood; 174A.

*Stem surface* (*young and mature*).—Dull and moderately covered with short, soft hairs and average of 1 mm in length and 157D in color.

*Branching*.—Freely branching, an average of 49 lateral branches.

*Stem size*.—An average of 15 cm in length and 2 mm in diameter.

*Stem strength*.—Very strong.

*Stem aspect*.—Stems grow in all directions from nearly horizontal to vertical.

Foliage description:

*Leaves*.—Compound, trifoliate to palmate division, broad ovate in overall shape, alternate arrangement, an average of 1.3 cm in length and 1.5 cm in width, internode length an average of 5 mm.

*Leaflets*.—3 to 5, narrow obovate to oblanceolate in shape, about 60% of trifoliate leaf center leaflets are trifid, giving those leaves a palmate-like overall leaf shape, acute to apiculate apex, attenuate base, entire margin, an average of 1 cm in length and 2.5 mm in width, color; young upper surface 143A, young lower surface 144A, mature upper surface 146A, mature lower surface 147B, upper and lower surface slightly glossy, upper very sparsely pubescent and lower surface and margins sparsely pubescent; hairs an average of 1 mm in length and 157D in color.

*Venation*.—Leaves; palmate, leaflets; pinnate, color; upper surface 146A and lower surface 147B.

*Stipules*.—Ovate in shape, an average of 5 mm in length and 2 mm in width, color; upper and lower surface 199A, surface sparsely pubescent.

*Petioles*.—An average of 0.5 mm in length, color; upper surface 151A and lower surface, leaflets sessile, surface sparsely pubescent.

Inflorescence description:

*Inflorescence type*.—Solitary, terminally and axillary placed along the stems.

*Flower number*.—An average of 7 per main stem.

*Flower fragrance*.—None.

*Flower longevity*.—About 5 days, self-cleaning.

*Flower type*.—Single, rotate.

*Flower aspect*.—Upright to outward.

*Flower size*.—An average of 2.4 cm in diameter and 8 mm in depth.

*Peduncles*.—An average of 5 mm in length and 1 mm in diameter, held at an average angle of 15° to lateral branches, moderately strong, 145B to 145C in color with 186D towards the tip, surface sparsely pubescent.

*Pedicels*.—None.

*Flower buds*.—Flattened globular in shape, an average of 6 mm in length and 7 mm in diameter prior to opening, color; 8C with base 166B.

*Sepals*.—10, 5 ovate and 5 oblong in shape, rotate arrangement, entire margin, acute apex, upper and lower surfaces; smooth and dull, ovate sepals; broadly cuneate base, an average of 5 mm in length and 3 mm in width, ovate sepals color; immature upper surface 174B to 174C with base 150B, immature lower surface 178A with base 150B, mature upper surface 174B to 174C with base 150B, mature lower surface 150B with apex 151B, oblong sepals; cuneate base, an average of 6 mm in length and 2 mm in width, oblong sepals color; immature upper and lower surface 144B, mature upper surface 144B, mature lower surface 143B.

*Calyx*.—Rotate, flat shape, an average of 3 mm in length and 13 mm in diameter.

*Petals*.—An average of 5 per flower, self-cleaning, rotate arrangement, orbicular to broadly obovate in shape, upper and lower surface glabrous and dull, entire margin, cuneate base, obtuse apex, an average of 10 mm in length and 9.5 mm in width, color; upper surface when opening 33A to 33B, lower surface when opening 11A, upper surface when fully open N30B to N30C suffused with 17D at the petal base and veins, lower surface when fully open 10A to 10B, color does not fade.

*Pistils*.—An average of 30, stigma flattened in shape, an average of 2 mm in diameter and 153B in color, style is an average of 1 mm in length and 0.5 mm in width, 153D in color, ovary is 148B in color and densely covered with short soft hairs 0.75 mm in length and 155A in color.

*Stamens*.—An average of 25 per flower, filaments are an average of 1 mm in length and 153D in color, anthers are flattened, ovate in shape, an average of 1 mm in length, an average of 0.75 mm in width and 11A in color, pollen is very sparse in quantity, too minimal to obtain a color reading.

*Seed*.—None observed.

It is claimed:

1. A new and distinct cultivar of *Dasiphora* plant named 'Hachdon' as herein illustrated and described.

* * * * *